United States Patent [19]

Chafetz et al.

[11] Patent Number: 4,663,348

[45] Date of Patent: May 5, 1987

[54] FUROSEMIDE SALTS AND PHARMACEUTICAL PREPARATIONS THEREOF

[75] Inventors: Lester Chafetz, New Providence; Jose Philip, Mendham, both of N.J.

[73] Assignee: Warner-Lambert Co., Morris Plains, N.J.

[21] Appl. No.: 751,763

[22] Filed: Jul. 2, 1985

[51] Int. Cl.$^4$ .................... A61K 31/34; C07D 307/54
[52] U.S. Cl. ...................................... 514/471; 549/494
[58] Field of Search .......................... 549/494; 514/471

[56] References Cited

U.S. PATENT DOCUMENTS

| | | | |
|---|---|---|---|
| 3,058,882 | 10/1962 | Sturm et al. | 514/471 |
| 3,565,920 | 2/1971 | Werner | 549/494 |
| 4,131,678 | 12/1978 | Amachler et al. | 544/295 X |
| 4,324,779 | 4/1982 | Dahihausen et al. | 424/20 |
| 4,564,625 | 1/1986 | Muschaweck et al. | 549/494 X |

FOREIGN PATENT DOCUMENTS 2134770 1/1972 Fed. Rep. of Germany .
2210607 7/1974 France .

*Primary Examiner*—Richard L. Raymond
*Attorney, Agent, or Firm*—Sandra M. Person

[57] ABSTRACT

Quaternary ammonium salts of furosemide are stable and highly water-soluble, affording thereby solid oral dosage forms which are more bioavailable, oral liquid dosage forms hitherto unavailable, and injectable dosage forms of furosemide with higher concentration, hence lower volume, which do not add to the sodium ion burden of patients to whom it may be administered.

6 Claims, No Drawings

FUROSEMIDE SALTS AND PHARMACEUTICAL PREPARATIONS THEREOF

BACKGROUND

Furosemide is 4-chloro-N-furfuryl-5-sulfamoylanthranilic acid. It is recognized in *United States Pharmacopeia* (USP) as a diuretic and used in medical practice as a diuretic, antihypertensive and antihypercalcemic agent. Its usual pharmaceutical dosage forms are Furosemide Injection, containing 10 mg per ml of furosemide as the sodium salt, and Furosemide Tablets, declaring 20-, 40- or 80-mg per tablet of furosemide.

Injection and tablet dosage forms, which are highly objectionable to many patients, are employed to administer furosemide because of its low solubility in water. Furosemide is listed in USP as being practically insoluble in water, which denotes a solubility less than 0.1 mg per ml.

THE INVENTION

It has been discovered that certain onium salts of furosemide, specifically, quaternary ammonium salts thereof, such as those made using choline, betaine, tetraalkylammonium, tetraaryl ammonium, aralkylammonium and alkarylammonium salts and hydroxides have potential for providing delivery systems for furosemide which are more pharmaceutically useul, more physically and chemically stable, and more bioavailable.

The furosemide saalts made in accordance with the invention have significantly higher water solubilities than furosemide. For example, furosemide choline salt has a solubility in water of about 770 mg per ml, which is equivalent to furosemide in solution at a concentration of about 590 mg per ml in water.

OBJECTS OF THE INVENTION

It is an object of the invention to provide furosemide salts of the general formula

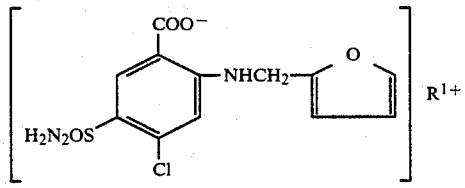

wherein $R^1$ is a moiety derived from at least one quaternary ammonium compound of formula II as set out below.

Useful ammonium compounds conform to the following formula:

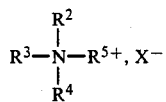

wherein $R^2$, $R^3$, $R^4$ and $R^5$ are independently selected from alkyl, aryl or other moiety linked via a carbon atom to the nitrogen atom; and X, when present, is a hydroxyl or halide moiety. Mixtures of such compounds are operable.

It is generally preferred that $R^2$ through $R^5$ be selected such that they are organic groups which do not contain substituents which would significantly interfere with the functionality of the ammonium nitrogen.

It is another object to provide pharmaceutical preparations containing one or more compounds of formula I.

It is yet another object to provide a process for preparing water soluble furosemide salts, which process comprises the step of contacting furosemide with at least one quaternary ammonium reactant under suitable conditions.

ADVANTAGES OF THE INVENTION

The furosemide derivatives of the invention possess several advantages over prior art forms of this drug.

Since bioavailability is proportional to the dissolution rate of a drug in water, the bioavailability of these furosemide derivatives in solid oral dosage forms is greater than that of furosemide in solid oral dosage forms.

R. E. Cutler and A. D. Blair, *Clinical Pharmacokinetics*, 4, 279–296 (1979) concluded that commercial furosemide tablets are 60 to 69% bioavailable in healthy subjects and 43 to 46% bioavailable in uremic patients as compared with formulations for injection.

Furthermore, more stable solid oral pharmaceutical dosage forms can be made from furosemide choline salt and analogous compounds. Furosemide is known to be very unstable in acidic media and chemically stable in alkaline media; c.f. J. E. Cruz et al., *International Journal of Pharmaceutics* 2, 275–281 (1979) and A. G. Ghanekar et al., *Journal of Pharmaceutical Sciences*, 67, 808–811 (1978).

Since the pH of a saturated solution of furosemide choline salt is about 8.2, it is basic and would be expected to be stable.

Intravenous delivery systems containing the salts of the invention are superior to those containing the sodium salt of furosemide, heretofore used, because the drug is a naturetic and because a higher concentration of furosemide can be obtained, allowing a lower volume of fluid to be injected with the same effect.

The compounds of the invention can be used in liquid oral dosage forms because of their water solubility. Patients who cannot readily swallow tablets have been forced, up until now, to use intravenous injection. A 1.0 percent furosemide choline salt solution has a pH of about 6.8 and would, therefore, be suitable as an ingredient in a syrup, elixir, or other suitable partially or wholly liquid system.

Other aspects and advantages of the invention will become apparent after a consideration of the following description of the invention.

DESCRIPTION OF THE INVENTION

The invention relates to novel water soluble salts of furosemide and their use in pharmaceutical formulations.

PREPARATION OF DERIVATIVES

The salts produced in accordance with the invention are prepared by reacting furosemide with one or more nitrogen-containing reactants, i.e., suitable nitrogen bases, which, under suitable conditions, yield cationic, i.e., quaternary, ammonium moieties. Useful reactants include those which yield choline, betaine, tetra-alkyl ammonium, arylalkyl ammonium, or tetraaryl ammonium residues and the like.

By "alkyl" is meant substituted and unsubstituted moieties containing groups conforming to the formula $C_nH_{2n+1}$. Generally, $C_{1-20}$, and preferably $C_{1-8}$, alkyl moieties are contemplated.

By "aryl" is meant substituted and unsubstituted moieties containing groups having aromatic character. Generally, $C_{6-30}$ and, preferably $C_{6-12}$, aromatic groups, e.g., substituted and unsubstituted phenyl groups.

The substituents on the aryl/alkyl groups of the nitrogen-containing reactant to be reacted with furosemide may be any moieties which, when present, do not significantly alter the chemical function of that reactant, e.g., hydroxyl groups, carboxyl groups, and the like.

By "suitable conditions" is meant that the salts are preferably prepared in the presence of reagents and using temperatures and pressures which facilitate the reaction.

Useful reagents can include potassium chloride, sodium chloride, and the like. In general alkaline reagents are preferred. Alkali metal halides are highly preferred. Potassium chloride is one particularly preferred reagent. Mixtures of such reagents can be used.

The temperatures and pressures employed in carrying out the invention are not critical. In general, temperatures of about 25° C. to about 40° C. are useful. Pressures may vary within wide limits, with those between about 0.5 atmosphere and about 3 atmospheres being typical.

While solventless reactions are contemplated, the reactions generally take place in the presence of one or more solvents. Useful reaction solvents include $C_{1-20}$ polar compounds, with $C_{1-10}$ alcohols preferred. Methanol and other alkanols are highly preferred solvents. Mixtures of solvents can be used.

Following reaction, the desired furosemide compound(s) can be precipitated or salted out of an oily filtration residue using a highly polar solvent. Useful highly polar solvents include acetone, ethanol, and the like. Mixtures of solvents are useful.

Other conventional recovery techniques can be used in combination with, or instead of, any of the techniques outline above.

PHARMACEUTICAL PREPARATIONS

The furosemide compounds produced in accordance with the invention are usually salts whose saturated solutions have pH's in the range of about 6.5 to about 8.5. As such, they are highly useful in the preparation of intravenous and oral dosage forms, among others.

Oral formulations containing the novel derivatives can also contain one or more of a variety of conventional excipients. Thus, additives such as colorants, sweeteners, stabilizers, binders, carriers and the like, can be present. One preferred group of additives are carriers, among which starch and lactose are exemplary. Such additives will generally be present in oral compositions at concentrations of about 60 to about 80 wt.%, based on the weight of the total composition.

A liquid oral dosage form of furosemide is made feasible by the good aqueous solubility of the furosemide derivatives, e.g., the choline salt. No liquid oral formulation of furosemide now exists, and patients who are unable to swallow tablets are repeatedly subjected to intravenous injection.

A 1 percent (w/v) aqueous solution of furosemide choline salt has a pH of about 6.8. It is a simple matter to prepare a syrup or elixir from such a solution which would be pharmaceutically attractive and from which the drug will be rapidly absorbed into the bloodstream after ingestion.

A preferred syrup composition based upon one inventive salt would contain, per liter:

| Ingredient | Amount |
| --- | --- |
| Furosemide choline salt | 11.10 g |
| Sorbitol Solution, USP 70% | 150.00 ml |
| Invert Sugar (50–60% Inverted) | 800.00 g |
| Glycerin, USP | 50.00 ml |
| D & C Red #33 Acid Fuchsine K 7057 | 0.016 g |
| Caramel, Acid Proof | 1.04 g |
| Menthol, USP | 0.03 g |
| Creme Vanilla Flavor PFC 8484 | 4.00 ml |
| Peppermint Stick Flavor PFC 8558 | 4.00 ml |
| Water, Potable, q.s. to | 1000.00 ml |

Potassium citrate or other suitable reagent can be added to adjust the pH to about 8, if desired.

This formulation is illustrative only and should not be read as limiting the invention to the particular combination of ingredients contained therein.

Injectable preparations containing the novel derivatives of the invention can be supplied as ready-to-use solutions or as solid or liquid concentrates to be mixed with water, or one or more other suitable media prior to use. Water, with or without other media, will generally comprise about 20 to about 30 wt.% of injectable formulations.

In a preferred embodiment, a USP furosemide injection is made by dissolving furosemide in water for injection with the aid of sodium hydroxide to obtain a concentration of furosemide of 10 mg/ml. This product crystallizes at refrigerator temperature (25° C.), so that its concentration at room temperature (about 4° C.) must be close to saturation. A simple solution of about 13.1 mg per ml of furosemide choline salt in water for injection will be physically stable, deliver 10 mg per ml of furosemide and contains no sodium ion. Higher concentrations can be used with the pH of solutions of the furosemide quaternary salt close to that of blood. A saturated solution of furosemide choline salt in water has a pH of 8.2.

The invention can be better understood via consideration of the following example.

The choline salt of furosemide was prepared by reacting furosemide with potassium hydroxide and choline chloride in a 1:1:1 mole ratio in methanol. 3.3 g furosemide, 0.56 g, potassium hydroxide and 1.39 g choline chloride were put into a 250 ml flask. 80 ml methanol was added and mixed in a sonicator until all reactants went into solution. The mixture was then filtered through a fine filter funnel and the solvent evaporated. The oily residue was treated with acetone to get a precipitate. The precipitate was twice recrystallized from a 50/50 mixture of 2-propanol and ethanol. The crystalline material was collected and dried in a vacuum oven at 70° C. Properties: white crystalline solid, M.p. 172.0°–173.5° C.

Structure:

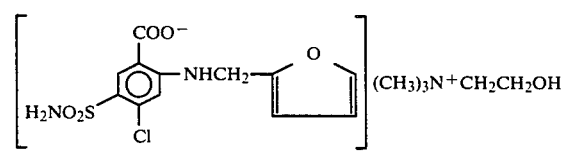

Molecular weight: 433.5.

Elemental analysis: Calculated for $C_{17}H_{24}ClN_3O_6S$: C-47.05; H-5.53; N-9.68; Cl-8.18; S-7.38.

Found: C-47.14; H-5.57; N-9.44; Cl-8.48; S-7.66.

Reasonable variations, such as those which would occur to a skilled artisan, can be made herein without departing from the scope of the invention.

We claim:

1. Compounds derived from furosemide which correspond to the general formula:

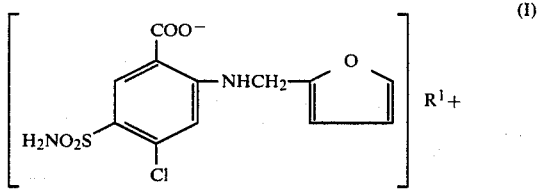

wherein $R^1$ is a moiety derived from at least one quaternary ammonium salt or hydroxide selected from the group consisting of: choline, betaine, tetraalkylammonium, alkyl aryl ammonium and tetraaryl ammonium salts and hydroxides wherein any alkyl or aryl moiety is optionally substituted with an —OH or —COOH group.

2. A compound in accordance with claim 1 wherein $R^1$ contains a choline residue.

3. A compound in accordance with claim 1 wherein $R^1$ contains a betaine residue.

4. A pharmaceutical preparation containing an effective amount of one or more of the compounds of claim 1 and at least one excipient.

5. A pharmaceutical preparation containing an effective amount of the compound of claim 2 and at least one excipient.

6. A pharmaceutical preparation containing an effective amount of the compound of claim 3 and at least one excipient.

* * * * *